(12) United States Patent
Ye et al.

(10) Patent No.: US 11,077,225 B2
(45) Date of Patent: Aug. 3, 2021

(54) HOLLOW POROUS SPHERICAL PARTICLE ARTIFICIAL BONE AS WELL AS PREPARATION METHOD AND APPLICATION THEREOF

(71) Applicant: SOUTH CHINA UNIVERSITY OF TECHNOLOGY, Guangzhou (CN)

(72) Inventors: Jiandong Ye, Guangzhou (CN); Fupo He, Guangzhou (CN)

( * ) Notice: Subject to any disclaimer, the term of this patent is extended or adjusted under 35 U.S.C. 154(b) by 0 days.

(21) Appl. No.: 16/725,861

(22) Filed: Dec. 23, 2019

(65) Prior Publication Data

US 2020/0129663 A1 Apr. 30, 2020

Related U.S. Application Data

(63) Continuation of application No. PCT/CN2018/111612, filed on Oct. 24, 2018.

(30) Foreign Application Priority Data

Feb. 9, 2018 (CN) .......................... 201810133103.3

(51) Int. Cl.
  *A61F 2/28* (2006.01)
  *A61L 27/56* (2006.01)
  (Continued)

(52) U.S. Cl.
  CPC ............... *A61L 27/12* (2013.01); *A61F 2/28* (2013.01); *A61L 27/3608* (2013.01);
  (Continued)

(58) Field of Classification Search
  CPC ...... A61L 27/12; A61L 27/3608; A61L 27/54; A61L 27/56; A61L 27/20; A61L 2430/02;
  (Continued)

(56) References Cited

U.S. PATENT DOCUMENTS 6,416,774 B1 7/2002 Radin et al.
2003/0191533 A1* 10/2003 Dixon .................... A61L 27/04
623/17.14

(Continued)

FOREIGN PATENT DOCUMENTS

CN 103113129 A 5/2013
CN 103893829 A 7/2014

(Continued)

OTHER PUBLICATIONS

Internation Search Report of PCT/CN2018/111612, dated Jan. 22, 2019.

*Primary Examiner* — Bruce E Snow
*Assistant Examiner* — Melissa A Hoban
(74) *Attorney, Agent, or Firm* — Erson IP (Nelson IP)

(57) ABSTRACT

The disclosure provides a preparation method of a hollow porous spherical particle artificial bone. The method comprises: (1) uniformly mixing bioceramic powder, bioglass powder and an excipient to obtain a solid-phase mixture, then adding binder solution to the solid-phase mixture, and uniformly mixing to obtain a plastic wet material; (2) loading a plastic wet material into an extrusion device of an extrusion rounder to be extruded by the orifice plate of the extrusion device to form a strip-shaped material; (3) putting the strip-shaped material into the spheronization device, cutting, and then spheronizing to form spherical particles; and (4) placing the spherical particles into a furnace, debinding, removing the excipient and the binder, and then sintering at 750-1550° C.

8 Claims, 1 Drawing Sheet

(51) Int. Cl.
   *A61L 27/12* (2006.01)
   *A61L 27/36* (2006.01)
   *A61L 27/54* (2006.01)

(52) U.S. Cl.
   CPC .............. *A61L 27/54* (2013.01); *A61L 27/56* (2013.01); *A61F 2310/00293* (2013.01)

(58) Field of Classification Search
   CPC .. A61L 27/10; A61F 2/28; A61F 2310/00293; A61F 2002/30968; A61F 2002/2835; A61F 2/3094
   See application file for complete search history.

(56) References Cited

U.S. PATENT DOCUMENTS

| | | | |
|---|---|---|---|
| 2008/0133026 A1 | 6/2008 | Barry et al. | |
| 2009/0051082 A1 | 2/2009 | Shunsuke et al. | |
| 2013/0236513 A1* | 9/2013 | Guelcher | A61K 38/1875 424/400 |
| 2015/0137404 A1* | 5/2015 | Tuchinskiy | B22F 7/06 264/46.1 |
| 2016/0015483 A1* | 1/2016 | Kumar | A61C 8/0075 606/301 |
| 2019/0083681 A1* | 3/2019 | Bhumiratana | A61L 27/50 |

FOREIGN PATENT DOCUMENTS

| | | |
|---|---|---|
| CN | 106390190 A | 2/2017 |
| CN | 106563170 A | 4/2017 |
| CN | 108324987 A | 7/2018 |
| EP | 1516635 A1 | 3/2005 |

\* cited by examiner

HOLLOW POROUS SPHERICAL PARTICLE ARTIFICIAL BONE AS WELL AS PREPARATION METHOD AND APPLICATION THEREOF

CROSS-REFERENCE TO RELATED APPLICATIONS

This application is a continuation of International Patent Application No. PCT/CN2018/111612 with a filing date of Oct. 24, 2018, designating the United States, now pending, and further claims priority to Chinese Patent Application No. 201810133103.3 with a filing date of Feb. 9, 2018. The content of the aforementioned applications, including any intervening amendments thereto, are incorporated herein by reference.

TECHNICAL FIELD

The disclosure relates to the field of artificial bone materials, and particularly to a hollow porous spherical particle artificial bone as well as a preparation method and application thereof.

BACKGROUND OF THE PRESENT INVENTION

Critical bone defects caused by trauma, infection, osteonecrosis and bone tumor are usually required for bone transplantation. In addition to autogenous bone and allogeneic bone grafts which are derived from limited sources, artificially synthesized bone repair materials (artificial bones) are more and more widely applied in clinic because of their wide sources, low price, convenient design and control on components and structures of materials. Among them, the most commonly used artificial bone in clinic is calcium phosphate ceramic, silicate ceramic, calcium carbonate ceramic, calcium sulfate ceramic, calcium phosphate cement, phosphate bioglass, silicate bioglass materials and the like. The artificial bone is usually used for bone defect repairing in the form of blocks or particles. The blocky artificial bone has relatively good mechanical properties, and can be used for repairing the bone defect of low- or moderate-load-bearing sites after being processed according to the shape of the bone defect. However, the sintered ceramic materials are difficult to process, and the shapes of bone defects are different, therefore it is difficult for the blocky materials to sufficiently fill the defect sites, resulting in limited clinical application of blocky artificial bones to a certain extent. Particle artificial bones can be randomly and sufficiently filled in bone defect sites without limitation from shapes of the bone defects and are more favored by orthopedic clinicians. The particle artificial bones have disadvantage of poor mechanical support, and are mainly used for the repairing of bone defects at non-load-bearing or low-load-bearing sites. Artificial bone particles mainly include irregular non-spherical particles and spherical particles. The non-spherical particles are mainly obtained by breaking large blocky materials and have poor flowability, and their sharp edges may damage surrounding tissues after being implanted into the body. The spherical particles have good flowability and are easy to operate, and can realize arbitrary accumulation of spheres after being filled in bone defect sites. According to an arbitrary sphere accumulation principle, microspheres can form three-dimensional interconnected pores, which is conducive to the growth of blood vessels and bone tissues. In addition, a study shows that an inflammatory response generated by implanting spherical particles into the body is significantly smaller than that of non-spherical particles.

At present, methods for preparing the spherical particle artificial bone mainly include a liquid drop condensation method and a microemulsion method. Adoption of the liquid drop condensation method can obtain spherical materials with large size (>1 mm) and small size distribution range, but it is difficult to prepare the small spherical materials. Adoption of the microemulsion method can prepare spherical materials with different particle size ranges, but the process is more complex and difficult to control the size distribution of the spherical materials. The spherical materials prepared by using the two methods have the problem of low yield. Although the spherical particles filled in the bone defect sites can obtain a completely three-dimensional interconnected pore structure, the porosity is low (<40%). Manufacturing of a porous structure in the spherical particles by adding a pore forming agent method, a gas foaming method and other methods can accelerate the degradation of artificial bones and facilitate the repairing and reconstruction of bone defects. A large number of studies have shown that the artificial bone with a macropore-micropore structure has a better bone repair effect.

In summary, the porous spherical particle artificial bone with the macropore-micropore structure has unique advantages in the aspect of non-load-bearing bone defect repair. However, technologies for preparing porous spherical particles has the problems of complex process, low yield, and difficulty in controlling sphere diameters and sphere diameter distribution and the like.

SUMMARY OF PRESENT INVENTION

In order to overcome the above disadvantages and shortages of the prior art, the objective of the disclosure is to provide a preparation method of a hollow porous spherical particle artificial bone. The preparation method is simple and does not need to add the pore forming agent. By adjusting and controlling the content of the excipient and sintering condition, the hollow size in the spherical particle and the pore sizes of the macropores and micropores in the shell can be adjusted and controlled.

Another objective of the disclosure is to provide the hollow porous spherical particle artificial bone prepared by the above preparation method. The hollow porous spherical particle artificial bone is of a hollow structure and meanwhile has a large number of macropores and micropores distributed in the shells of the spherical particles. The hollow porous spherical particle artificial bone is controllable in pore structure, high in porosity and high in strength.

Still another objective of the disclosure is to provide the hollow porous spherical particle artificial bone prepared by the preparation method.

The objectives of the disclosure are realized by the following technical solution:

A preparation method of a hollow porous spherical particle artificial bone, comprising the following steps:

(1) uniformly mixing bioceramic powder, bioglass powder and an excipient to obtain a solid-phase mixture, then adding binder solution to the solid-phase mixture, and uniformly mixing to obtain a plastic wet material;

wherein, in the solid-phase mixture, the mass fraction of the excipient is 10%-85%; the mass ratio of bioceramic to bioglass sintering additive is 0.01-100;

the mass ratio of the binder to solid-phase mixture is 0.2-3;

(2) loading the plastic wet material obtained in step (1) into an extruder, extruding through the orifice plate to form a strip-shaped wet material;

(3) transferring the strip-shaped wet material obtained in step (2) into a spheronizer, cutting, and then spheronizing to form spherical particles;

(4) placing the spherical particles obtained in step (3) into a furnace, debinding to remove the excipient and the binder, and then sintering at 750-1550° C. to obtain the hollow porous spherical particle artificial bone.

The bioceramic powder in step (1) is more than one of hydroxyapatite powder, calcium phosphate powder, silicate powder, calcium carbonate powder or calcium sulfate powder.

The bioglass powder in step (1) is phosphate glass powder or silicate glass powder.

The excipient in step (1) is at least one of microcrystalline cellulose, methyl cellulose, lactose, monosaccharide, cyclodextrin, starch, alginate, chitosan, pectin ester acid, carrageenin, polyacrylate, polyvinylidene alcohol, carboxymethyl cellulose, xanthan gum and polyvinylpyrrolidone.

The debinding in step (4) is debinding at 300-750° C.

The canal size of the orifice plate of the spheronizer in step (2) is 0.3-3 mm.

The hollow porous spherical particle artificial bone obtained by the preparation method of the hollow porous spherical particle artificial bone is of a hollow spherical shell structure, and macropores and micropores are distributed in the spherical shell.

The size of center hollow cavity of the spherical particle is 50-1200 μm; the size of the macropores in the spherical shell is 10-200 μm, and the size of the micropores in the spherical shell is 0.1-10 μm.

The disclosure also provides application of the hollow porous spherical particle artificial bone in repairing bone defect sites.

Compared with the prior art, the disclosure has the following advantages and beneficial effects:

(1) in the disclosure, the porous spherical particle artificial bone simultaneously having hollow and hierarchical pore structures is prepared by utilizing the principle that bioglass forms a liquid phase during the sintering and the liquid phase wraps a gas. This preparation method is simple and does not need to add the pore forming agent. By adjusting the content of the excipient and the sintering condition, the hollow size in the spherical particle and the pore diameters of the macropores and micropores in the shell can be adjusted and controlled.

(2) The hollow porous spherical particle artificial bone prepared by the method of the disclosure has high sphericity degree, large yield and narrow size distribution range; the size of the hollow porous spherical particle artificial bone can be adjusted and controlled within a large size range (from micron level to millimeter level) by adjusting the canal diameter of the orifice plate of the extruder, the content of excipient, sintering temperature and the like.

(3) The hierarchical pore and hollow structure of the hollow porous spherical particle artificial bone prepared by the method of the disclosure contribute to promote the degradation of materials and the ingrowth of cells and bone tissues, thereby promoting osteogenesis; the hollow porous spherical particle provides high porosity and large specific surface area, and is suitable for use as a carrier for drugs and growth factors.

DETAILED DESCRIPTION OF PREFERRED EMBODIMENTS

The disclosure will be further described in detail in conjunction with examples, but embodiments of the disclosure are not limited thereto.

Example 1

The preparation method of the hollow porous spherical particle artificial bone in this example comprises the following steps:

(1) β-tricalcium phosphate powder, phosphate glass ($50P_2O_5$-$2ZnO$-$28CaO$-$20Na_2O$) and microcrystalline cellulose were mixed uniformly to obtain a solid-phase mixture. The mass fraction of microcrystalline cellulose was 50%, and the mass ratio of β-tricalcium phosphate to phosphate glass was 3:1. 0.5% methylcellulose solution was prepared, slowly added into the solid-phase mixture (the mass ratio of the solution to the solid-phase mixture was 0.85) and uniformly mixed, so as to obtain a wet material with good plasticity;

(2) the plastic wet material in step (1) was put into the extruder (the canal diameter of the extrusion orifice plate was 1.5 mm) to obtain a strip-shaped material;

(3) the strip-shaped material obtained in step (2) was transferred to the spheronizer, cut into short column-shaped materials in the disc of spheronizer and then spheronized into spherical particles with a diameter of about 1.4 mm;

(4) the spherical particles obtained in step (3) were put into a high-temperature furnace, heated to 700° C. at a heating rate of 1° C./min and holded for 2 hour to remove microcrystalline cellulose and methylcellulose, and then was heated to 1000° C. at a heating rate of 2° C./min and holded for 1 hour, thereby obtaining a hollow porous β-tricalcium phosphate/phosphate glass spherical particles artificial bone.

Figure 1:
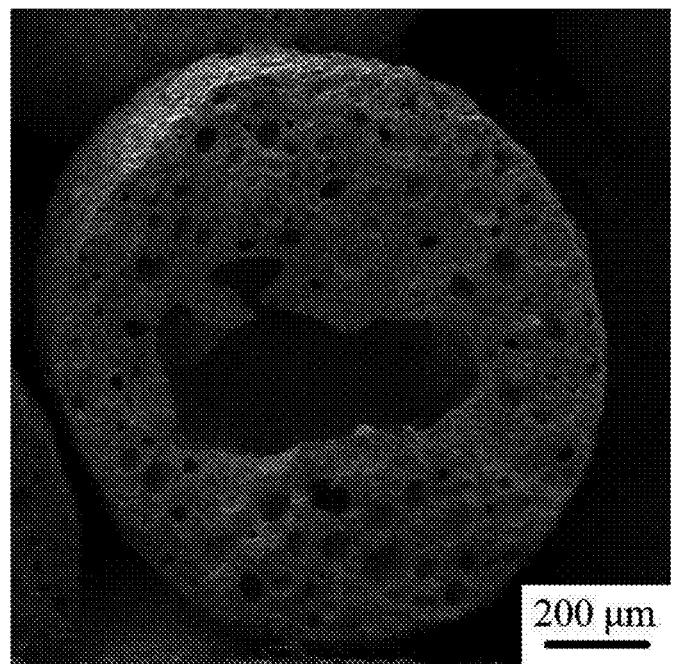
FIG. 1 is a scanning electron micrograph (SEM) of a hollow porous spherical particle artificial bone prepared according to example 1.

The hollow porous β-tricalcium phosphate/phosphate glass spherical particle artificial bone obtained in this example is shown in FIG. 1, is about 1.2 mm in sphere diameter, about 600 μm in central cavity size of spherical particle, about 20-110 μm in pore diameter of macropores in the shell, and about 0.5-8 μm in micropore size.

Example 2

The preparation method of the hollow porous spherical particle artificial bonein this example comprises the following steps:

(1) calcium carbonate powder, phosphate bioglass ($50P_2O_5$-$3SrO$-$12CaO$-$35Na_2O$) and microcrystalline cellulose were uniformly mixed to obtain a solid-phase mixture. The mass fraction of microcrystalline cellulose was 30%, and a mass ratio of calcium carbonate powder to phosphate bioglass was 1:1. 0.6% of methylcellulose solution was prepared, slowly added into the solid-phase mixture (a mass ratio of the solution to the solid-phase mixture was 0.85) and mixed uniformly, so as to obtain a wet material with good plasticity;

(2) the plastic wet material in step (1) was put into the rounding device of the extrusion rounder (the pore diameter of the extrusion orifice plate was 1.5 mm) to obtain a strip-shaped material;

(3) the strip-shaped material obtained in step (2) was loaded into the rounding device of the extrusion rounder, cut into short column-shaped materials in a rounding disc and then rounded into spherical particles with a diameter of about 1.4 mm;

(4) the spherical particles obtained in step (3) were put into a high-temperature furnace, heated to 700° C. at a heating rate of 1° C./min and then preserved for 2 h, microcrystalline cellulose and methylcellulose were removed, and then the remaining substance was heated to 1000° C. at a heating rate of 2° C./min and preserved for 1 h, thereby obtain a hollow porous calcium carbonate/phosphate glass spherical particle artificial bone.

The hollow porous calcium carbonate/phosphate glass spherical particle artificial bone obtained in this example is 1.4 mm in a diameter, about 150 μm in the central cavity size of the spherical particle, about 50-100 μm in pore diameter of macropores in the shell, and about 0.5-8 μm in a micropore size.

Example 3

The preparation method of the hollow porous spherical particle artificial bone in this example comprises the following steps:

(1) the Cu-containing calcium silicate powder, silicate bioglass ($45SiO_2$-$26CaO$-$17Na_2O$-$5P_2O_5$-$7B_2O_3$), starch and microcrystalline cellulose were uniformly mixed to obtain a solid-phase mixture. The mass fraction of starch and microcrystalline cellulose was 45%, the mass ratio of starch to microcrystalline cellulose was 1:3, and the mass ratio of tricalcium silicate to silicate bioglass was 2:1. 0.6% hydroxypropyl cellulose solution was prepared, slowly added into the solid-phase mixture (the mass ratio of the solution to the solid-phase mixture was 0.8) and uniformly mixed, so as to obtain a wet material with good plasticity;

(2) the plastic wet material in step (1) was put into the extrusion device of the extrusion rounder (the hole diameter of the extrusion orifice plate was 2 mm), to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 1.9 mm;

(4) the spherical particles obtained in step (3) were put into a high-temperature furnace, heated to 650° C. at a heating rate of 0.9° C./min and then preserved for 2 h, starch, microcrystalline cellulose and hydroxypropyl cellulose were removed, and then the remaining substance was heated to 1120° C. at a heating rate of 1° C./min and preserved for 2 h, thereby obtaining a hollow porous calcium silicate/silicate bioglass spherical particle artificial bone.

The hollow porous calcium silicate/silicate bioglass spherical particle artificial bone obtained in this example is 1.65 mm in diameter, about 250 μm in the central cavity size of the spherical particle, about 20-90 μm in pore diameter of macropores in the shell, and about 0.5-10 μm in micropore size.

Example 4

The preparation method of the hollow porous spherical particle artificial bone in this example comprises the following steps:

(1) Sr-containing calcium silicate powder, l-tricalcium phosphate, phosphate bioglass ($48P_2O_5$-$25CaO$-$27Na_2O$), cyclodextrin and microcrystalline cellulose were uniformly mixed to obtain a solid-phase mixture. The total mass fraction of cyclodextrin and microcrystalline cellulose was 55%, the mass ratio of starch to microcrystalline cellulose was 1:2, and the mass ratio of Sr-containing calcium silicate to β-tricalcium phosphate to silicate bioglass was 1:1:1. 0.6% polyvinyl alcohol solution was prepared, slowly added into the solid-phase mixture (the mass ratio of the solution to the solid-phase mixture was 0.9) and then uniformly mixed, so as to obtain a wet material with good plasticity;

(2) the plastic wet material in step (1) was put into the extrusion device of the extrusion rounder (the hole diameter of the extrusion orifice plate was 0.5 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 0.5 mm;

(4) the spherical particles obtained in step (3) were put into a high-temperature furnace, heated to 650° C. at a heating rate of 0.5° C./min and then preserved for 2 h, cyclodextrin, microcrystalline cellulose and polyvinyl alcohol were removed, and then the remaining substance was heated to 1100° C. at a heating rate of 2° C./min and preserved for 2 h, thereby obtaining a hollow porous calcium silicate/β-tricalcium phosphate/phosphate bioglass spherical particles artificial bone.

The hollow porous calcium silicate/β-tricalcium phosphate/phosphate bioglass spherical particle artificial bone obtained in this example is 0.4 mm in diameter, about 100 μm in the central cavity size of the spherical particle, about 10-50 μm in pore diameter of macropores in the shell, and about 0.3-10 μm in micropore size.

Example 5

The preparation method of the hollow porous spherical particle artificial bone in this example comprises the following steps:

(1) hydroxyapatite, phosphate bioglass ($45P_2O_5$-$2CuO$-$33CaO$-$20Na_2O$), lactose and microcrystalline cellulose were mixed uniformly to obtain a solid-phase mixture. The total mass fraction of lactose and microcrystalline cellulose was 70%, the mass ratio of lactose to microcrystalline cellulose was 1:1, and the mass ratio of hydroxyapatite to phosphate bioglass was 4:1. 0.5% sodium alginate solution was prepared, slowly added into the solid-phase mixture (the mass ratio of the solution to the solid-phase mixture was 0.95) and then uniformly mixed, so as to obtain a wet material with good plasticity;

(2) the plastic wet material in step (1) was loaded into the extrusion device of the extruder (the hole diameter of the extrusion orifice plate was 1.5 mm) to obtain a strip-shaped material;

(3) the strip-shaped material obtained in step (2) was loaded into the rounding device of the extrusion rounder, cut into short column-shaped material in the rounding disc and then rounded into spherical particles with a diameter of about 1.5 mm;

(4) the spherical particles obtained in step (3) were put into a high temperature furnace, heated to 400° C. at a heating rate of 0.7° C./min and then preserved for 2 h, sodium alginate, lactose and microcrystalline cellulose were removed, and then the remaining substance was heated to 1200° C. at a heating rate of 2° C./min and then preserved for 2 h, thereby obtaining a hollow porous hydroxyapatite/phosphate bioglass spherical particles artificial bone.

The hollow porous hydroxyapatite/phosphate bioglass spherical particle artificial bone obtained in this example is 1.25 mm in diameter, about 300 μm in the central cavity size of the spherical particle, about 20-100 μm in pore diameter of macropores in the shell, and about 0.1-10 μm in micropore size.

Example 6

The preparation method of the hollow porous spherical particle artificial bone in this example comprises the following steps:

(1) Mg-doped hydroxyapatite, calcium carbonate, phosphate bioglass ($45P_2O_5$-$35CaO$-$20Na_2O$), sodium alginate and microcrystalline cellulose were mixed uniformly to obtain a solid-phase mixture. The total mass fraction of sodium alginate and microcrystalline cellulose was 60%, the mass ratio of sodium alginate to microcrystalline cellulose was 1:20, and the mass ratio of Mg-doped hydroxyapatite to calcium carbonate to phosphate bioglass was 2:2:2. 3% gelatin solution was prepared, slowly added into the solid-phase mixture (the mass ratio of the solution to the solid-phase mixture was 0.9) and then uniformly stirred, so as to obtain a wet material with good plasticity;

(2) the plastic wet material in step (1) was loaded into the extrusion device of the extruder rounder (the hole diameter of the extrusion orifice plate was 1.5 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 1.5 mm;

(4) the spherical particles obtained in step (3) were put into a high-temperature furnace, heated to 400° C. at a heating rate of 0.8° C./min and preserved for 2 h, sodium alginate, microcrystalline cellulose and gelatin were removed, and then the remaining substance was heated to 1250° C. at a heating rate of 2° C./min and preserved for 2 hours, thereby obtaining a hollow porous hydroxyapatite/calcium carbonate/phosphate bioglass spherical particle artificial bone.

Figure 2:
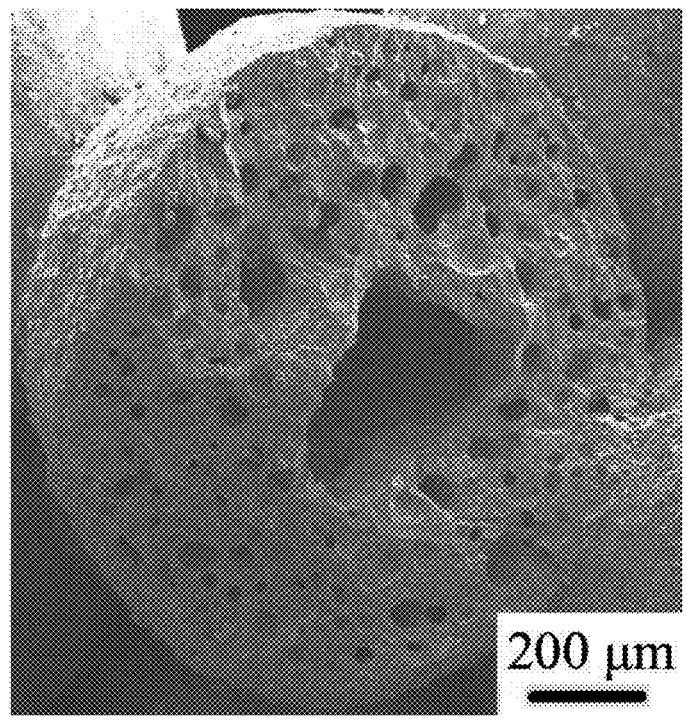
FIG. 2 is an SEM of a hollow porous spherical particle artificial bone prepared according to example 6.

The hollow porous hydroxyapatite/calcium carbonate/phosphate bioglass spherical particle artificial bone in this example is shown in FIG. 2, is 1.25 mm in diameter, about 300 μm in the central cavity size of the spherical particle, about 20-100 μm in pore diameter of macropores in the shell, and about 0.1-10 μM in micropore size.

Example 7

The preparation method of the hollow porous spherical particle artificial bone in this example comprises the following steps:

(1) akermanite, silicate bioglass ($44SiO_2$-$28CaO$-$16Na_2O$-$4P_2O_5$-$8B_2O_3$), polypyrrolidone and microcrystalline cellulose were uniformly mixed to obtain a solid-phase mixture. The total mass fraction of polypyrrolidone and microcrystalline cellulose was 25%, the mass ratio of lactose to microcrystalline cellulose was 1:4, and the mass ratio of akermanite to silicate bioglass was 2:1. 0.75% polyvinyl butyral solution was prepared, slowly added into the solid-phase mixture (the mass ratio of the solution to the solid-phase mixture was 0.65) and uniformly mixed, so as to obtain a wet material with good plasticity;

(2) the plastic wet material in step (1) was loaded into the extrusion device of the extrusion rounder (the hole diameter of the extrusion orifice plate was 1 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 1 mm;

(4) the spherical particles obtained in step (3) were put into a high-temperature furnace, heated to 600° C. at a heating rate of 2° C./min and preserved for 2 h, polypyrrolidone, microcrystalline cellulose and polyvinyl butyral were removed, and then the remaining substance was heated to to 1200° C. at a heating rate of 5° C./min and preserved for 3 h, thereby obtaining a hollow porous akermanite/silicate bioglass spherical particles artificial bone.

The hollow porous akermanite/silicate bioglass spherical particle artificial bone obtained in this example is 0.85 mm in diameter, about 50 μm in the central cavity size of the spherical particle, about 20-50 μm in pore diameter of macropores in the shell, and about 0.2-10 μm in micropore size.

Example 8

The preparation method of the hollow porous spherical particle artificial bone in this example comprises the following steps:

(1) magnesium hydroxyapatite, β-tricalcium phosphate, phosphate bioglass ($46P_2O$-$8MgO$-$26CaO$-$20Na_2O$), polypyrrolidone and pectin ester acid were mixed uniformly to obtain a solid-phase mixture. The total mass fraction of polypyrrolidone and pectin ester acid was 70%, the mass ratio of polypyrrolidone to pectin ester acid was 1:1, the mass ratio of hydroxyapatite to 3-tricalcium phosphate to phosphate Bioglass was 2:3:2. 0.2% sodium alginate solution was prepared, slowly added into the solid-phase mixture (the mass ratio of the solution to the solid-phase mixture was 1) and uniformly mixed, so as to obtain a wet material with good plasticity;

(2) the plastic wet material in step (1) was loaded into the extrusion device of the extrusion rounder (the hole diameter of the extrusion orifice plate was 0.5 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 0.5 mm;

(4) the spherical particles obtained in step (3) were put into a high-temperature furnace, heated to 700° C. at a heating rate of 0.75° C./min and preserved for 3 h, polypyrrolidone, pectin ester acid and sodium alginate were removed, and then the remaining substance was heated to 1100° C. at a heating rate of 4° C./min and preserved for 2 h, thereby obtaining a hollow porous hydroxyapatite/β-tricalcium phosphate/phosphate bioglass spherical particle artificial bone.

The hollow porous hydroxyapatite/β-tricalcium phosphate/phosphate bioglass spherical particle artificial bone in this example is 0.38 mm in diameter, about 100 μm in the central cavity size of the spherical particle, about 10-60 μm in pore diameter of macropores in the shell, and about 0.2-10 μm in micropore size.

Example 9

The preparation method of the hollow porous spherical particle artificial bone in this example comprises the following steps:

(1) calcium silicate, magnesium silicate, silicate bioglass ($45SiO_2$-$2SrO$-$27CaO$-$14Na_2O$-$5P_2O_5$-$7B_2O_3$) and microcrystalline cellulose were uniformly mixed. The total mass fraction of microcrystalline cellulose was 48%, and the mass ratio of calcium silicate to magnesium silicate to silicate bioglass was 2:1:2. 0.1% xanthan gum solution was prepared, slowly added into the solid-phase mixture (the mass ratio of the solution and the solid-phase mixture was 0.8) and uniformly mixed, so as to obtain a wet material with good plasticity;

(2) the plastic wet material in step (1) was loaded into the extrusion device of the extrusion rounder (the hole diameter of the extrusion orifice plate was 3 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 3 mm;

(4) the spherical particles obtained in step (3) were put into a high-temperature furnace, heated to 720° C. at a heating rate of 1° C./min and preserved for 2 h, microcrystalline cellulose and xanthan gum were removed, and then the remaining substance was heated to 1120° C. at a heating rate of 2° C./min and preserved for 2 h, thereby obtaining a hollow porous calcium silicate/magnesium silicate/silicate bioglass spherical particle artificial bone.

The hollow porous calcium silicate/magnesium silicate/silicate bioglass spherical particle artificial bone obtained in this example is 2.2 mm in diameter, about 1200 μm in the central cavity size of the spherical particle, about 35-200 μm in pore diameter of macropores in the shell, and about 0.25-10 μm in micropore size.

Example 10

The preparation method of the hollow porous spherical particle artificial bone in this example comprises the following steps:

(1) hydroxyapatite, α-tricalcium phosphate, phosphate bioglass ($45P_2O_5$-$10SrO$-$32CaO$-$20Na_2O$) and microcrystalline cellulose were mixed uniformly to obtain a solid-phase mixture. The total mass fraction of microcrystalline cellulose was 60%, and the mass ratio of hydroxyapatite to α-tricalcium phosphate to phosphate bioglass was 2:1:1. 0.6% methylcellulose solution was prepared, slowly added into the solid-phase mixture (the mass ratio of the solution to the solid-phase mixture was 0.9) and uniformly mixed, so as to obtain a wet material with good plasticity;

(2) the plastic wet material in step (1) was loaded into the extrusion device of the extrusion rounder (the hole diameter of the extruding orifice plate was 0.5 mm) to obtain a strip-shaped material;

(3) the strip-shaped material obtained in step (2) was loaded into the rounding device of the extrusion rounder, cut into short column-shaped materials in the rounding disc and then rounded into spherical particles with a diameter of about 0.5 mm;

(4) the spherical particles obtained in step (3) were put into a high-temperature furnace, heated to 680° C. at a heating rate of 1° C./min and preserved for 3h, microcrystalline cellulose was removed, and then the remaining substance was heated to 1120° C. at a heating rate of 3° C./min and preserved for 2 h, thereby obtaining a hollow porous hydroxyapatite/α-tricalcium phosphate/phosphate bioglass spherical particle artificial bone.

The hollow porous hydroxyapatite/α-tricalcium phosphate/phosphate bioglass spherical particle artificial bone is 0.4 mm in diameter, about 120 μm in the central cavity size of the spherical particle, about 20-65 μm in pore diameter of macropores in the shell, and about 0.1-10 μm in micropore size.

The excipient microcrystalline cellulose in the above examples can also be replaced by more than one of microcrystalline cellulose, methylcellulose, lactose, monosaccharide, cyclodextrin, starch, alginate, chitosan, pectin ester acid, carrageenan, polyacrylate, polyethyleneglycol, carboxymethylcellulose, xanthan gum, and polyvinylpyrrolidone.

The above examples are preferred embodiments of the disclosure, but the embodiments of the disclosure are not limited to the above examples. Any other changes, modifications, substitutions, combinations and simplifications made without departing from the spiritual essence and principles of the disclosure should be equivalent replacement manners and are included within the scope of protection of the disclosure.

We claim:

1. A preparation method of a hollow porous spherical particle artificial bone, comprising the following steps:
    (1) uniformly mixing bioceramic powder, bioglass powder and an excipient to obtain a solid-phase mixture, then adding binder solution to the solid-phase mixture and uniformly mixing to obtain a plastic wet material;
    wherein, in the solid-phase mixture, the mass fraction of the excipient is 10%-85%; the mass ratio of bioceramic to a glass sintering additive is 0.01-100;
    the mass ratio of the binder to solid-phase mixture is 0.2-3;
    (2) loading the plastic wet material obtained in step (1) into an extrusion device of an extrusion rounder to be extruded by an orifice plate of the extrusion device to form a strip-shaped material;
    (3) putting the strip-shaped material obtained in step (2) into an spheronization device, cutting, and then spheronizing to form spherical particles; and
    (4) placing the spherical particles obtained in step (3) into a furnace, debinding, removing the excipient and the binder, and then sintering at 750-1550° C. to obtain a hollow porous spherical particle artificial bone,
    wherein the artificial bone is of a hollow spherical shell structure, and macropores and micropores are distributed on the spherical shell.

2. The preparation method of the hollow porous spherical particle artificial bone according to claim 1, wherein the bioceramic powder in step (1) is more than one of hydroxyapatite powder, calcium phosphate powder, silicate powder, calcium carbonate powder or calcium sulfate powder.

3. The preparation method of the hollow porous spherical particle artificial bone according to claim 1, wherein the bioglass powder in step (1) is phosphate glass powder or silicate glass powder.

4. The preparation method of the hollow porous spherical particle artificial bone according to claim 1, wherein the excipient in step (1) is at least one of microcrystalline cellulose, methyl cellulose, lactose, monosaccharide, cyclodextrin, starch, alginate, chitosan, pectin ester acid, carrageenin, polyacrylate, polyvinylidene alcohol, carboxymethyl cellulose, xanthan gum and polyvinylpyrrolidone.

5. The preparation method of the hollow porous spherical particle artificial bone according to claim 1, wherein the debinding in step (4) is debinding at 300-750° C.

6. The preparation method of the hollow porous spherical particle artificial bone according to claim 1, wherein the pore canal of the orifice plate of the rounding device of the extrusion rounder in step (2) is 0.3-3 mm.

7. The preparation method of the hollow porous spherical particle artificial bone according to claim 1, wherein a center hollow cavity of the spherical particle is 50-1200 μm in size; the pore size of the macropores on the spherical shell is 10-200 μm, and the pore size of the micropores on the spherical shell is 0.1-10 μm.

8. Application of the hollow porous spherical particle artificial bone prepared by the preparation method according to claim 1 in repairing bone defect sites.

* * * * *